United States Patent [19]

Bellotti et al.

[11] 4,142,974

[45] Mar. 6, 1979

[54] APPARATUS FOR MEASURING ULTRAFILTRATION DURING DIALYSIS WITH LONGITUDINALLY MOVABLE AND CLAMPABLE RETENTION MEMBER

[75] Inventors: Marc Bellotti, Winnetka; William J. Schnell, Wheeling; John M. Munsch, Libertyville, all of Ill.

[73] Assignee: Baxter Travenol Laboratories, Inc., Deerfield, Ill.

[21] Appl. No.: 851,664

[22] Filed: Nov. 15, 1977

[51] Int. Cl.² .............................................. B01D 31/00
[52] U.S. Cl. .................................... 210/94; 210/321 A
[58] Field of Search .................. 210/241, 249, 321 A, 210/321 R, 321 B, 96 M, 85, 94

[56] References Cited

U.S. PATENT DOCUMENTS 3,289,846  12/1966  Warrington et al. ............ 210/321 A
3,809,246  5/1974   Niogret ............................. 210/241 X
3,976,574  8/1976   White ............................... 210/321 A Primary Examiner—John Adee
Attorney, Agent, or Firm—Garrettson Ellis; Paul C. Flattery

[57] ABSTRACT

An improved valving system is provided in a dialysis system in which the dialysis solution flow path through the dialyzer may be sealed off adjacent the inlet and outlet of the dialyzer, with the pumped dialysis solution being shunted so that the pump and heater do not need to be turned off. As ultrafiltration takes place over a predetermined period of time, it can be directly measured by monitoring the liquid level of a reservoir connected to the sealed portion of the dialysis solution flow path. The dialysis unit itself is held in a bracket which defines the valving system by means of a longitudinally movable and clampable retention member for bearing against the top of and holding the dialyzer member.

2 Claims, 9 Drawing Figures

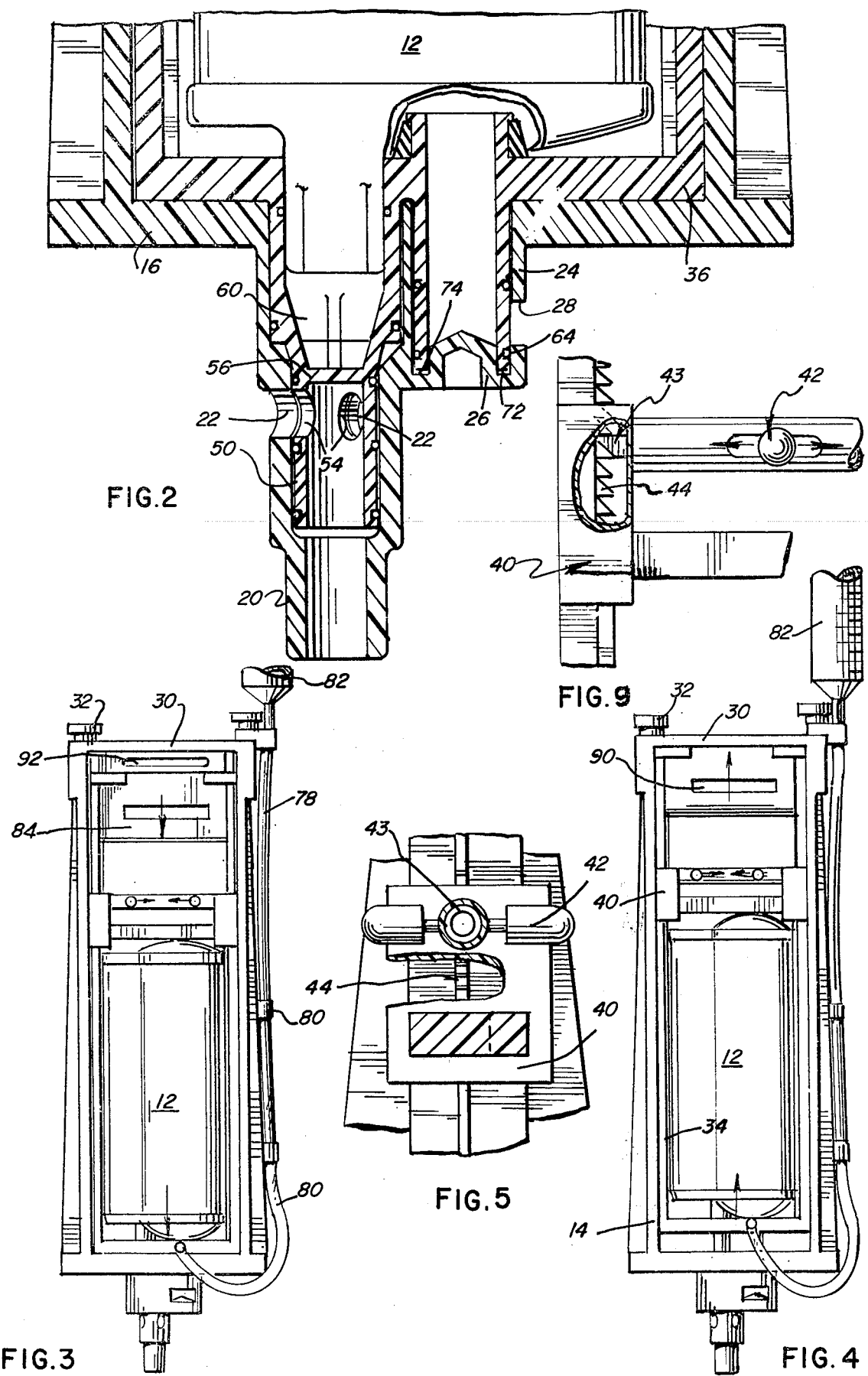

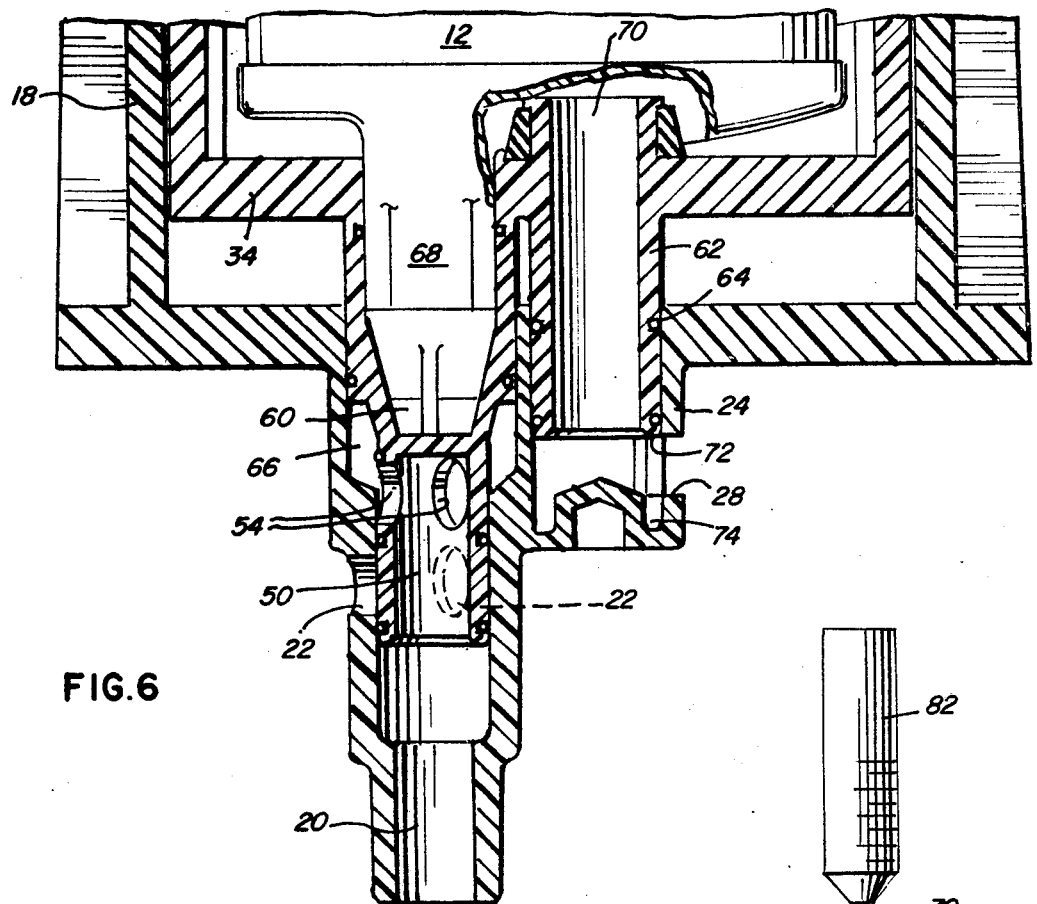
FIG. 6
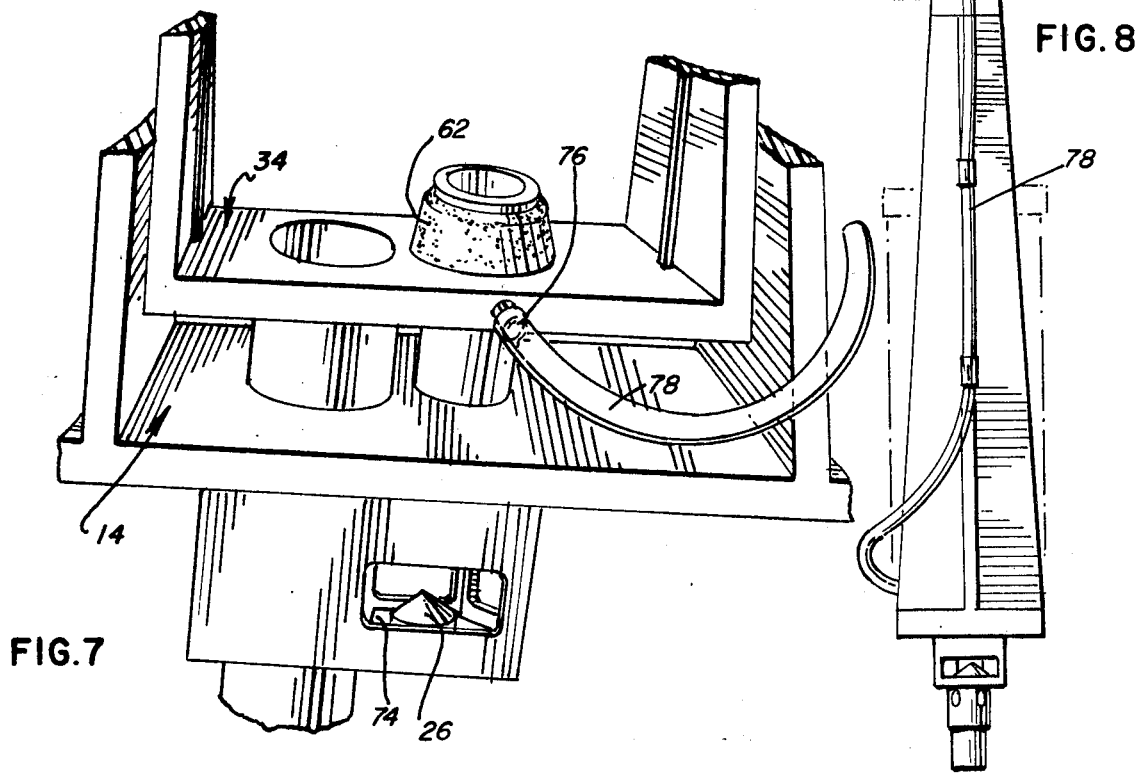
FIG. 7
FIG. 8

APPARATUS FOR MEASURING ULTRAFILTRATION DURING DIALYSIS WITH LONGITUDINALLY MOVABLE AND CLAMPABLE RETENTION MEMBER

BACKGROUND OF THE INVENTION

In U.S. application Ser. No. 787,983, filed Apr. 15, 1977 by Richard P. Goldhaber, a method and apparatus for determining ultrafiltration during dialysis is shown. Basically, a membrane dialyzer unit is placed on a mounting in dialysis apparatus. The mounting comprises a horizontal sliding valve connected to the inlet and the outlet of the dialyzer. Accordingly, by sliding the dialyzer and the valve into one valving position, the dialysis solution passes through the valve into the inlet and out of the outlet of the dialyzer. When the dialysis unit and the sliding valve are moved in the other horizontal sliding position, both the inlet and the outlet of the dialyzer unit are sealed. Since blood can still pass through the dialysis unit, ultrafiltration still takes place causing liquid to rise in a reservoir communicating with the sealed portion of the dialysis solution flow path, to measure ultrafiltration.

However, in practical use, certain disadvantages of construction have been found in this apparatus. For example, the horizontal sliding valve of the Goldhaber application comprises first and second sliding members positioned against each other in sliding relation, specifically to pivot back and forth into the open and closed valving positions. This valve has been found to be particularly difficult to seal, since the O-rings surrounding the respective valve orifices tend to be moved out of position, since the sliding valve members pivot in a plane which is parallel to the plane of the sealing O-rings. It has been found that in order to obtain effective sealing, the pressure between the two valve members must be so great as to run a risk of dislodging the O-ring, or not being able to slide the valve at all, and causing undue wear as the dialysis unit valve member is operated.

In accordance with this invention, an ultrafiltration monitoring device for use in a dialyzer is provided which exhibits more reliable long-term operation, since the O-rings are positioned so that the direction of sliding valving motion in the apparatus of this invention is perpendicular to the plane of the O-ring rather than parallel thereto as in the previous application. Accordingly, better sealing and more reliable sealing for a longer period of time is provided.

Also, the ultrafiltration testing device of this invention utilizes a novel, longitudinally movable and clampable retention member for bearing against the top of and holding a dialyzer member within the device of this invention.

DESCRIPTION OF THE INVENTION

In accordance with this invention, a bracket for a membrane dialysis unit is provided in which the dialysis unit defines blood inlet and outlet ports, a dialysis solution inlet port, and a dialysis solution outlet port. The bracket is adapted to be carried by a conventional dialyzer unit which provides dialysis solution for use in the membrane dialyzer unit.

The improved bracket of this invention comprises a first frame which defines a first tubular flow conduit defining a first lateral aperture, and a second flow conduit defining a closed outer end and a second lateral aperture.

The bracket also includes a second frame, carried by the first frame, and adapted for relative axial sliding movement between first and second positions with respect to the first frame. The second frame is adapted for carrying the membrane dialyzer. The second frame also defines a third tubular flow conduit positioned in telescoping relation with the first flow conduit. The third flow conduit defines third lateral aperture means comprising one or more spaced apertures, and a wall obstructing the bore of the third tubular conduit positioned inwardly of the third lateral aperture means.

The second frame also defines a fourth tubular flow conduit positioned in telescoping relation with the second flow conduit.

The third and fourth flow conduits are respectively adapted to communicate with the inlet and outlet of a membrane dialyzer unit carried by the second frame.

The apertures defined above are positioned so that, in the first sliding position, the first lateral aperture is sealed by the third flow conduit, and the third aperture means is positioned to permit fluid communication through the third conduit, through the third aperture means, and around the bore-obstructing wall in a flow path adapted to lead through a dialyzer mounted therein. In this position, the fourth conduit is spaced to permit fluid flow through the fourth conduit and the second lateral aperture, typically for the outlet of dialysis solution.

The apparatus is also proportioned so that in the second sliding position the third lateral aperture means provides fluid communication with the first lateral aperture means, and is otherwise sealed to prevent fluid flow in the flow path adapted to lead through the mounted dialyzer, and the fourth flow conduit is positioned to prevent flow therethrough and through the second conduit.

Accordingly, in the first sliding position, a sealed flow path is provided through the bracket of this invention for communication with both the inlet and the outlet of a dialyzer mounted therein. In the second sliding position, the inlet and outlet of the dialyzer are sealed to prevent flow, while flow through the dialyzer inlet can be shunted through the first lateral aperture means for recirculation. A liquid volume measuring conduit is also provided to measure in direct manner the increase in liquid volume in the sealed dialysis solution conduit over a predetemined time period.

The bracket of this invention may be used with recirculating single pass type dialysis solution delivery systems such as the Travenol RSP dialyzer. Also, it may be used in conjunction with other dialysis solution delivery systems in which the dialysis solution is automatically made from concentrate, and processed in the apparatus prior to delivery through the dialyzer unit.

The bracket of this invention also carries conduit means in communication with the portion of the dialysis solution flow path which is capable of being sealed by the bracket of this invention. The conduit means is adpated to communicate with flow measuring means, so that the increase of the liquid volume within the sealed dialysis solution flow path, due to ultrafiltration, can be measured.

Accordingly, the bracket of this invention is used by connecting it to a dialysis solution delivery apparatus and, in turn, connecting a dialyzer unit to the bracket member.

The dialysis procedure can proceed in a normal manner, while the bracket of this invention occupies its first position as defined above.

When it is desired to measure the rate of ultrafiltration which is taking place in the dialysis procedure, the bracket is simply moved to its second position by pushing the first and second frames together. By this act, both the dialysis solution inlet and outlet to the dialyzer unit may be sealed, while a shunt aperture is opened for incoming dialysis solution so that the dialysis solution pump and heater of the delivery system do not have to be shut off. Spontaneously, over a measured period of time, the liquid level in the conduit and the connected fluid measuring device will rise, to provide a direct measure of ultrafiltration over any desired time period, without any adjustment of the flow of blood through the system, or the pumping of dialysis solution.

When the ultrafiltration rate has been measured, the flow of dialysis solution to the dialyzer unit is reinstituted by simply moving the first and second frame back into the first position again.

Referring to the drawings,

FIG. 2 is a longitudinal sectional view of the lower end of the bracket of this invention, showing the channels and ports recited above in the second position.

FIG. 3 is an elevational view of the bracket of this invention in the second position, when flow of dialysis solution through the dialyzer unit is blocked, and dialysis solution is being shunted.

FIG. 4 is an elevational view of the bracket of this invention in the first position, when dialysis solution can be circulated through the dialyzer unit mounted therein.

FIG. 5 is a fragmentary, elevational view, with parts broken away, taken along line 5—5 of FIG. 1.

FIG. 6 is a vertical sectional view of the lower end of the bracket of this invention, similar to FIG. 2, but with the parts shown in the first position, permitting flow through the dialysis unit.

FIG. 7 is a fragmentary, perspective view of the lower portion of the bracket of this invention.

FIG. 8 is an elevational view of the bracket of this invention, similar to FIG. 4, but rotated 90 degrees about its longitudinal axis.

FIG. 9 is a fragmentary sectional view, rotated by 90 degrees, of FIG. 5.

Figure 1:
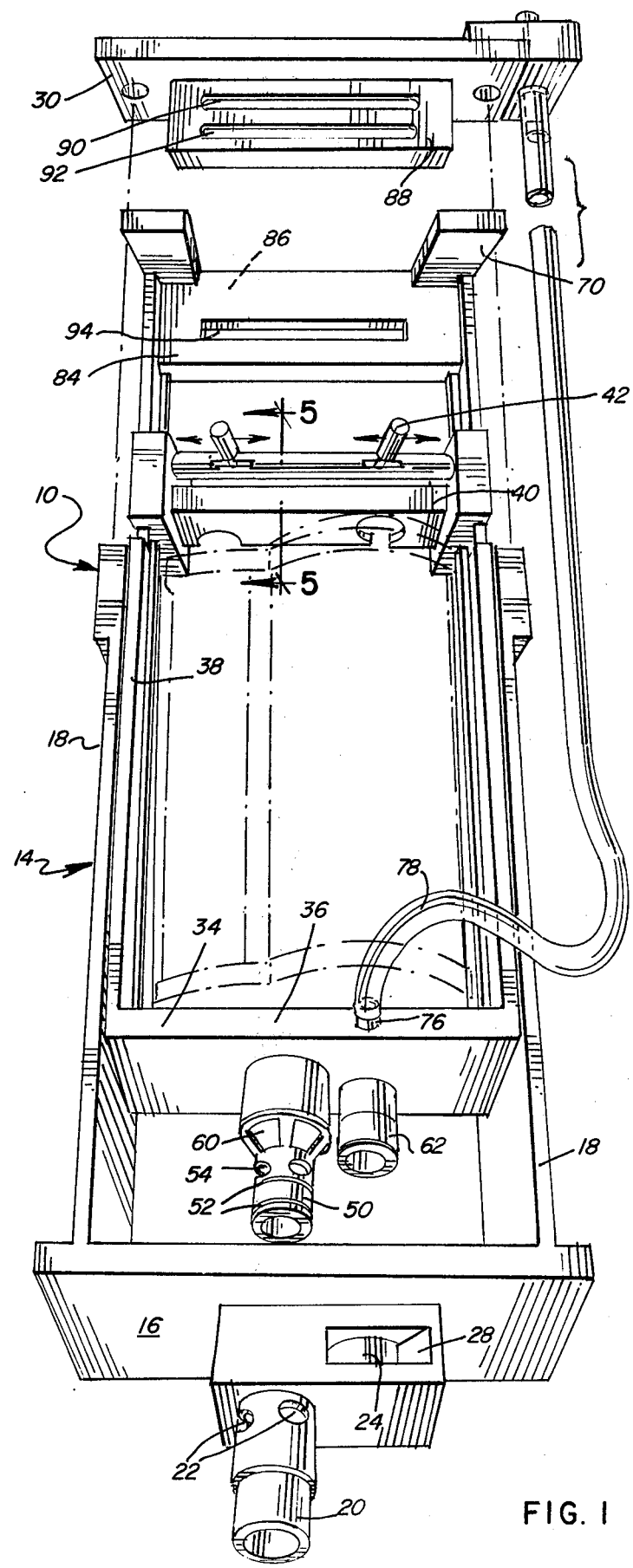
FIG. 1 is a perspective, exploded view of the bracket of this invention.

Referring to the drawings, a bracket 10 is provided for a membrane dialysis unit or the like, which is illustrated in the specific embodiment as coil dialyzer unit 12, specifically a CD dialyzer unit sold by Travenol Laboratories, Inc. of Deerfield, Illinois. However, the invention of this application may be adapted for use with other types of membrane dialysis units as well, including coil dialyzers wound with nonwoven screening, flat plate dialyzers in which a stack of separate membranes are utilized, convoluted membrane dialyzers, and hollow fiber dialyzers, or any geometry in which the dialysis flow compartment may be isolated.

The bracket of this invention defines a first frame 14 which may be made out of a single piece of plastic to have, as shown, a bottom plate 16 and a pair of side walls 18.

First frame 14 also defines a first tubular flow conduit 20 defining a first lateral aperture means, specifically embodied here as three equally spaced apertures 22. A second flow conduit 24 is also provided, defining a closed outer end 26 and second lateral aperture means 28. A top piece 30 is provided, being attachable to first frame 14 by thumbscrews 32.

Second frame 34 also defines a lower wall 36 and side wall 38, positioned to be carried within walls 18 of the first frame 14 in longitudinally slidable relationship thereto. Second frame 34 may be installed in the device, and then top member 30 may be secured in place to retain second frame 34 in its slidably carried position within the first frame.

Second frame 34 is proportioned to carry membrane dialyzer 12 as shown in FIG. 1. Sliding top member 30 comprises a pair of spring mounted handles 42 which control laterally protruding members 43 in a conventional manner which normally engage rack 44 mounted axially along the inner faces of walls 18 so that retention member 40 is fixably retained in its normal position, but can be disengaged from the rack 44 by squeezing of handles 42 and moved upwardly or downwardly to permit the installation of a dialyzer 12 and the retention thereof by placing the retention member firmly on the top of the dialyzer, and then allowing the retention member to once again engage rack 44.

Second frame 34 also includes a third tubular flow conduit 50, which is normally positioned in telescoping relation with the first flow conduit 20. O-rings 52 are provided on the outside of third conduit 50 to provide a seal between the two conduits.

The third flow conduit 50 defines one or more third lateral apertures 54; in this specific embodiment three of such apertures spaced to permit registry with apertures 22.

A wall 56 obstructs the bore of third conduit 50 at a position which is inward from the third lateral aperture means 54. Above wall 56, a plurality of windows 60 (i.e. four) are provided so that, in the first position, flow can pass through apertures 54 out of port 50, around wall 56, and back into third flow conduit 50 through windows 60.

Second frame 34 also defines a fourth tubular flow conduit 62, which may be positioned in telescoping relation with second flow conduit 24 as shown. O-rings 64 are provided for sealing of the junction between conduits 24 and 62.

FIG. 6 shows the configuration of the bracket of this invention in its first sliding position. First lateral apertures 22 are seen to be out of engagement with third lateral apertures 54 which, in turn, communicate with an enlarged space 66 outside of third conduit 50, so that dialysis solution passing through first conduit 20 may enter thrid conduit 50, passing through apertures 54, through space 66, into windows 60, and upwardly into the inlet 68 of dialyzer 12, which inlet is positioned in mating, telescoping relation with third conduit 60.

Circulated dialysis solution leaves the outlet aperture 70 of dialyzer 12, entering into fourth conduit 62, and from there passing out of the lower end of fourth conduit 62, briefly into second conduit 24, and out flow aperture 28, which may be adapted as shown to simply spill the spent dialysis solution back into the recirculating single pass type dialyzer system. Alternatively, for example when a single pass dialyzer is used, a conduit may be connected to aperture 28 to convey the dialysis solution away from the apparatus for discard or reprocessing as desired.

This is the configuration which is utilized for the usual dialysis mode while both blood and dialysis solution are passing through the dialyzer.

When the ultrafiltration rate is desired to be measured over a period of time, second frame 34 may be manually pushed downwardly, using push plates 70, attached to the second frame if desired, to bring the two frames into the position as indicated in FIG. 2. In this second position, the aperture means 54 communicates with the first lateral apertures 22. Accordingly, dialysis solution being pumped upwardly through first conduit 20 is prevented from flowing upwardly into dialyzer 12, and instead is shunted through apertures 22 for recirculation. If desired, conduits may be connected to apertures 22 for conveyance of the dialysis solution back to the storage tank.

Fourth conduit 62, in turn, is positioned so that its outer end 72 sealingly engages annular groove 74 defined in the end 26 of the second conduit 24. Accordingly, the dialysis solution outlet from the dialyzer 12 is correspondingly sealed.

An aperture 76 (FIG. 7) penetrates through the wall 34 for communication into the bore defined by fourth conduit 62, and tubing 78 is positioned in communication at one end with aperture 76. Tubing 78 may be carried by brackets 80, and leads upwardly to a vertically elevated position, where it is adapted for communication with a burette member 82 for measuring the increase of the liquid volume within the portion of the dialysis solution flow path sealed as shown in FIG. 2.

During normal operation, the liquid "head" will reside in tubing 78 at a level which approximates the upper edge of dialysis unit 12, varying from that ideal level by any pressure differential from atmospheric which may exist in the dialysis solution flow path of the dialysis unit. Accordingly, upon moving the bracket of this invention into the configuration of FIG. 2, as ultrafiltration continues, the liquid "head" will rise in tubing 78 and will spill into burette 82, to facilitate the measurement, over a period of a minute or so or as desired, of the rate of ultrafiltration in the dialysis process. This is accomplished without shutting off of the dialysis solution pump, heater, or the flow of blood through the dialyzer.

When it is desired to resume the flow of dialysis solution, the second frame may be pulled upwardly again to resume the position of FIG. 6. This can be accomplished by manually gripping the top 30 of the first frame and squeezing top member 84, which is attached to the second frame, to pull the entire second frame upwardly.

Top member 84 defines a slot 86, open at its upper edge, into which projecting plate 88, carried by top 30 of the first frame, can fit. A pair of preferably colored indicator members 90, 92 are positioned on projecting plate 88. Lateral slot 94 is defined in top member 84 and communicates with slot 86.

Indicator members 90, 92 are positioned so that in the first position of FIGS. 4 and 6, indicator member 90 may be visible through slot 94, and in the second position as shown in FIGS. 2 and 3, indicator member 92 may be visible. Indicator member 90 may carry the word "dialyze," while indicator 92 may carry the work "ultrafiltrate". The indicators may be of different prominent colors, so that the operating mode of the bracket of this invention may be readily determined by a quick glance.

The device of this invention is particularly useful for dialysis procedures with a high ultrafiltration rate ("hemofiltration"), since it is then essential to accurately monitor the ultrafiltration rate.

The above has been offered for illustrative purposes only, and is not for the purpose of limiting the invention of this application, which is as defined in the claims below.

That which is claimed is:

1. A bracket for a membrane dialysis unit in which said dialysis unit defines blood inlet and outlet ports, a dialysis solution inlet port, and a dialysis solution outlet port, the improvement comprising: a first frame, and a second frame carried by the first frame and adapted for relative axial sliding movement between first and second positions with respect to the first frame, and including means for carrying a membrane dialyzer, said first frame being adapted in the first sliding position to permit the flow of dialysis solution through said dialysis unit, and being adapted in the second sliding position to seal both the dialysis solution inlet port and outlet port of the dialysis unit, and means for measuring the increase of volume of liquid within the sealed flow path of said dialysis unit for measurement of ultrafiltration, in which said second frame also carries a longitudinally movable and clampable retention member for bearing against the top of and holding a dialyzer member positioned within said second frame.

2. The bracket for a membrane dialysis unit of claim 1 in which said retention member is a sliding top member which comprises spring-mounted handle means and laterally protruding members movable in response to said handle means, and rack means mounted on said second frame, to be engaged by said laterally protruding members for fixably retaining said sliding top member in a position against the top of a membrane dialysis unit, whereby said protruding members can be disengaged from the rack by manipulation of the handle means for disengagement from the membrane dialysis unit.

* * * * *